US012612348B2

(12) United States Patent
Cotti Comettini

(10) Patent No.: US 12,612,348 B2
(45) Date of Patent: Apr. 28, 2026

(54) PROCESS FOR PURIFYING A MIXTURE OF DIOLS

(71) Applicant: NOVAMONT S.P.A., Novara (IT)

(72) Inventor: Marco Cotti Comettini, Brusnengo (IT)

(73) Assignee: NOVAMONT S.P.A., Novara (IT)

( * ) Notice: Subject to any disclaimer, the term of this patent is extended or adjusted under 35 U.S.C. 154(b) by 649 days.

(21) Appl. No.: 18/000,539

(22) PCT Filed: Jun. 4, 2021

(86) PCT No.: PCT/EP2021/064993
§ 371 (c)(1),
(2) Date: Dec. 2, 2022

(87) PCT Pub. No.: WO2021/245228
PCT Pub. Date: Dec. 9, 2021

(65) Prior Publication Data
US 2023/0212099 A1 Jul. 6, 2023

(30) Foreign Application Priority Data
Jun. 4, 2020 (IT) ........................ 102020000013243

(51) Int. Cl.
*C07C 29/84* (2006.01)

(52) U.S. Cl.
CPC .................................. *C07C 29/84* (2013.01)

(58) Field of Classification Search
CPC .......... C07C 29/84; C07C 29/80; Y02E 50/10
See application file for complete search history.

(56) References Cited

U.S. PATENT DOCUMENTS

2014/0275465 A1    9/2014   Garikipati et al.

FOREIGN PATENT DOCUMENTS

| CN | 104640830 A | * | 5/2015 | ............. C07C 29/80 |
| CN | 105283431 A | * | 1/2016 | ........... B01D 61/025 |
| JP | 2013060429 A | * | 4/2013 | |
| JP | 2014193837 A | | 10/2014 | |
| WO | 2014152665 A1 | | 9/2014 | |
| WO | 2019102030 A1 | | 5/2019 | |

OTHER PUBLICATIONS

Chinese Office Action issued on Jan. 14, 2025 for corresponding Chinese Application No. 202180047419.0.
Japanese Office Action issued on Jan. 9, 2025 for corresponding Japanese Application No. 2022-574598.
International Search Report and Written Opinion issued on Sep. 17, 2021 for corresponding PCT Application No. PCT/EP2021/064993.
International Preliminary Report on Patentability issued on Aug. 26, 2022 for corresponding PCT Application No. PCT/EP2021/064993.

* cited by examiner

*Primary Examiner* — Deborah D Carr
(74) *Attorney, Agent, or Firm* — POLSINELLI PC

(57) ABSTRACT
The present invention relates to a process for the separation of 1,3 and 1,4-butanediol from a mixture thereof.

17 Claims, 1 Drawing Sheet

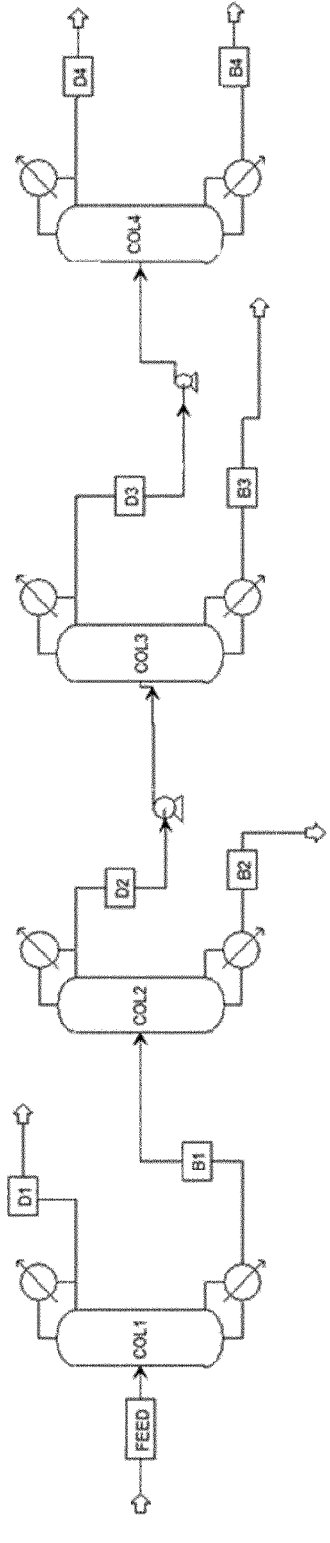

PROCESS FOR PURIFYING A MIXTURE OF DIOLS

CROSS-REFERENCE TO RELATED APPLICATIONS

This application is a national stage application (under 35 U.S.C. § 371) of PCT/EP2021/064993, filed Jun. 4, 2021, which in turn claims the benefit of Italian Application No. 102020000013243, filed Jun. 4, 2020, the disclosures of which are incorporated herein by reference in their entireties.

The present invention relates to a process for simultaneously purifying 1,3-butanediol and 1,4-butanediol from a mixture thereof.

1,3-butanediol (generally known as BG, 1,3-BG, 1,3-BDO or 1,3-butylene glycol) is a four-carbon diol with two stereoisomers: R-1,3-BDO and S-1,3-BDO. The racemic mixture is commonly used in many industrial processes, e.g. as an organic solvent for food flavouring agents or as a reagent for the production of polyurethane resins and polyesters. Due to its low toxicity and high tolerability it is also increasingly used in the cosmetics industry in personal care products, e.g. in the formulation of hair and bath products, eye and face make-up, perfumes, personal cleansing, shaving and skin care products. Optically active 1,3-BDO is also a widely used component of antibiotics, pheromones, fragrances and insecticides.

1,4-butanediol (generally known as 1,4-BDO, 1,4-BD or 1,4-butylene glycol) is widely used as a monomer for the production of various types of products such as, for example, polyesters of the diacid-diol type or as an intermediate for the synthesis of compounds such as gamma-butyrolactone and tetrahydrofuran. Because of their mechanical and processing properties, polyesters comprising repeating units derived from a dicarboxylic acid and a diol are now widely used in all fields of application of thermoplastic polymer materials such as films, moulded and blown articles and fibres. Moreover, it is preferable that the polyesters thus obtained are biodegradable, in particular according to EN 13432.

The chemical production of $C_2$-$C_4$ short-chain diols from fossil resources has been developed and optimised for decades. 1,3-BG is traditionally produced by a chemical process involving the hydration of acetylene to form acetaldehyde, which is then converted to 3-hydroxybutyraldehyde and reduced to form 1,3-BG. This usually results in the raceme form. 1,4-BDO can be synthesised by various chemical processes from petrochemical raw materials: acetylene, via ethynylation with formaldehyde; butadiene, via acetylation or halogenation; propylene, via epoxidation or oxyacetylation; n-butane, via formation of maleic anhydride and its subsequent hydrogenation by various routes.

Due to dwindling fossil resources, fluctuating oil prices and increasing environmental problems, the production of $C_2$-$C_4$ diols from renewable sources through biological processes has attracted considerable interest.

1,3-BG and 1,4-BDO can in fact be produced through fermentation processes from renewable sources such as carbohydrates, such as sugars and lignocellulosic biomass, or from synthetic gases (CO, $CO_2$ and/or $H_2$), directly (WO 2015/158716) or via the formation of bio-succinic acid (WO 2011/063055) and its subsequent hydrogenation or through the formation of polyhydroxyalkanoate (WO 2011/100601).

Patent application WO 2015/158716 describes a process for the production of 1,4-BDO comprising fermentation in a culture medium by a microorganism having at least one metabolic pathway for the synthesis of 1,4-BDO, in which said culture medium comprises a mixture of glucose and sucrose. Similarly, WO 2010/127319 describes a fermentation process for producing 1,3-BG from renewable sources.

However, 1,3-BG and 1,4-BDO produced from renewable sources generally contain impurities, including by-products deriving directly from fermentation and degradation processes. Such impurities need to be removed if the use of 1,3-BG and 1,4-BDO is to be ensured, for example in the cosmetic sector and in the synthesis of polyesters of the diacid-diol type, where purities higher than 99% for 1,3-BG and higher than 98%, preferably also higher than 99% for 1,4-BDO, are required respectively. In fact, in these sectors, the higher their level of purity the more monomers such as 1,3-BG and 1,4-BDO are sought after.

In addition, the above-mentioned fermentation processes generally employ different microorganisms and lead to the production of 1,3-BG and 1,4-BDO with different impurity contents, both in terms of quality and quantity.

For example, fermentatively produced 1,4-BDO may contain impurities including 1,4-BDO monoacetate, 2-(4-hydroxybutoxy) tetrahydrofuran, 2-pyrrolidone, tetrahydrofuran, 1,3-propanediol, gamma-butyrolactone, 1,6-hexanediol. Processes for purifying fermentatively produced 1,4-BDO are for example described in patent applications WO 2019/102030 and WO 2014/152665.

Fermentatively produced 1,3-BDO is usually obtained in a single enantiomeric form, typically the R-form, and may instead contain impurities including 3-hydroxy-butanal, 4-hydroxy-2-butanone, 3-hydroxybutoxy-2-butanone, 1,2-propanediol, 1,3-propanediol, 2,3-butanediol. Processes for purifying fermentatively produced 1,3-BG are for example described in patent application WO 2018/183628.

This means that purification processes that meet the requirements of each of the two diols and are adapted to the characteristics of each of the fermentation products need to be identified and implemented. The two diols 1,3-BG and 1,4-BDO in fact also have different physical properties and consequently require the use of different separation unit operations, or at least complex control of the operating conditions for each.

For this reason, although the fermentation processes for producing the two diols are similar and require essentially the same equipment, a process optimised for the purification of 1,3-BG is generally not suitable for the purification of 1,4-BDO and vice versa.

To overcome the problems described above, it has now surprisingly been found that it is possible to simultaneously purify the two diols from a mixture by a single process.

In fact, a process has been identified that allows the two compounds to be separated from their mixture, obtaining a level of purity of even >98% for each. In addition, this process allows 1,3-BG and 1,4-BDO to be purified and separated from other compounds in the mixture that may have physical properties similar to 1,3-BG and 1,4-BDO, including a boiling point higher than that of water (>100° C.), solubility in water or both.

Through the possibility of purifying the two compounds from a mixture thereof, they can also be produced simultaneously, in a mixture or separately, in the same production plant. Compared to separate production and purification campaigns for 1,3-BG and 1,4-BDO in the same plant, which require significant plant shutdowns in the transition from one to the other, this represents a significant advantage in terms of timing, costs as well as yields of products, as the products could deteriorate in case of prolonged storage.

A further advantage is the flexibility of the plant, which allows the purification of 1,3-BG and 1,4-BDO in variable ratios that are adaptable to market demands.

The process according to the present invention comprises in particular a step of distilling a mixture comprising 1,3-BG and 1,4-BDO and a subsequent step of distilling a fraction comprising 1,3-BG, making it possible to obtain a 1,3-BG composition having a concentration of said 1,3-BG above 99%, preferably above 99.5% by weight. Advantageously, said process at the same time also makes it possible to obtain a 1,4-BDO composition having a concentration of said 1,4-BDO above 98% by weight, more preferably above 99% by weight, even more preferably above 99.5% by weight.

In a first aspect, therefore, the present invention relates to a process for separating 1,3-BG and 1,4-BDO from a mixture thereof comprising a preliminary step of mixing the synthesis products of 1,3-butanediol and the synthesis products of 1,4-butanediol and comprising the further steps of:

(a) removing from that mixture, by one or more distillation operations,
        i. the solvent
        ii. a heavy fraction
        iii. a light fraction
        iv. a fraction including 1,4-BDO,
        in which at least one of said fractions (iii) and (iv) comprises 1,3-BG;
    (b) subjecting at least one of said fractions (iii) and (iv) comprising 1,3-BG to further distillation.

Said process makes it possible to obtain a 1,3-BG composition having a concentration of said 1,3-BG of more than 99% by weight at the end of step b). According to one aspect, the 1,3-BG obtained is a raceme. According to an alternative aspect, the 1,3-BG obtained has a higher content of R enantiomer than S enantiomer.

Through said process a 1,4-BDO composition having a concentration of said 1,4-BDO of more than 98% by weight, more preferably more than 99% by weight, even more preferably more than 99.5% by weight, can be obtained in sub-step iv of step a) or at the end of step b).

Starting from a mixture of the two diols, it is indeed surprisingly possible to obtain both 1,3-BG and 1,4-BDO at high levels of purity through a simple purification process consisting essentially of distillation operations.

These results are even more surprising in view of the fact that some impurities of 1,4-BDO form azeotropes with 1,3-BG. The number of distillation operations and the number of columns for each operation in each step of the process according to the invention is not particularly limiting.

The process according to the invention will be described in greater detail below.

FIG. 1 shows a diagram of a possible plant configuration relating to a preferred embodiment of the process.

Step a) may be performed by appropriately dimensioning the distillation system to effectively separate mixtures with different ratios of 1,3-BG and 1,4-BDO. Advantageously, the mixture fed to step a) of the process according to the invention comprises 1,3-BG and 1,4-BDO with 1,3-BG/1, 4-BDO weight ratios higher than 1/99, preferably higher than 1/33, more preferably higher than 1/24, more preferably higher than 1/15, even more preferably higher than 1/10 and below 99/1, preferably below 3/1, more preferably below 1/1, even more preferably below 1/2, even more preferably below 1/5.

The process comprises, prior to step a), a preliminary step of mixing the synthesis product of 1,3-BG and the synthesis product of 1,4-BDO, both comprising reaction by-products and/or impurities and optionally a solvent, in addition to said 1,3-BG and 1,4-BDO. Advantageously, some of said by-products and/or impurities and/or solvent are separated from the mixture of 1,3-BG and 1,4-BDO before process step a).

According to a preferred embodiment of the invention, the mixture comprising 1,3-BG and 1,4-BDO undergoing step a) of the process according to the invention results from the production of 1,3-BG and 1,4-BDO by fermentation. Such fermentative production may take place in separate fermenters, either simultaneously or at different times, resulting in the formation of a crude fermentation mixture; preferably production of the two diols takes place simultaneously in separate fermenters.

According to a preferred aspect, the process therefore comprises, before step a), a step of mixing the broths resulting from the fermentative production of 1,3-BG and 1,4-BDO (the so-called crude mixtures), resulting in a crude mixture comprising 1,3-BG and 1,4-BDO.

In this case, the process preferably further optionally comprises, prior to step a) and advantageously after the preliminary mixing step, a step of separating one or more fractions containing by-products and impurities from the crude mixture comprising 1,3-BG and 1,4-BDO, resulting in a mixture comprising 1,3-BG and 1,4-BDO.

According to a preferred embodiment, the process for separating 1,3-BG and 1,4-BDO from a mixture thereof is therefore preceded by the steps of.

1) mixing the broths from the fermentative production of 1,3-BG and 1,4-BDO to obtain a crude mixture comprising 1,3-BG and 1,4-BDO,
    2) separating one or more fractions comprising solvent, by-products and/or impurities from said crude mixture, resulting in a mixture comprising 1,3-BG and 1,4-BDO.

It is particularly advantageous to feed a homogeneous mixture of the two diols to the above-mentioned step 2) of the process according to the invention.

The production of 1,4-BDO from renewable sources by fermentation takes place, for example, according to the process described in WO 2015/158716.

In WO 2015/158716 the fermentation broth comprising 1,4-BDO from a renewable source and water is generally obtained by a fermentation process from a culture medium containing at least one sugar, preferably glucose, and optionally one or more sugars other than glucose, in the presence of one or more microorganisms having at least one metabolic pathway for the synthesis of 1,4-BDO.

The culture medium may comprise other substances necessary for growth and sustenance of the microorganism during the fermentation phase, such as elements such as C, H, O, N, K, S, P, Fe, Ca, Co, Mn, Mg. Typically, the culture medium may comprise one or more components selected from the group consisting of sugars other than glucose, protein hydrolysates, proteins, amino acids, organic acids, vitamins, mineral salts, yeast extracts, and trace elements such as cobalt, calcium and copper. Cobalt, calcium and copper can be dosed into the culture medium, for example, as salts such as cobalt chloride, calcium chloride and copper chloride. Generally, the culture medium comprises at least one sugar, usually glucose, and optionally one or more sugars other than glucose, in concentrations between 10 and 100 g/L. Since the microorganism consumes one or more sugars during the fermentation stage in the present process, it is generally necessary to add more of these sugars to the fermentation reactor. This addition may be made continuously or discontinuously, as known to those skilled in the art. The components of the culture medium, including sugars, protein hydrolysates, proteins, amino acids, organic acids, vitamins, minerals, yeast extracts and trace elements are typically added in excess of the microorganism's actual needs and, therefore, are not fully utilised and remain in the broth at the end of fermentation in the form of impurities.

To limit the content of unused sugars and thus optimise the economy of the process, the supply of one or more sugars is advantageously interrupted or gradually decreased before the end of fermentation. As regards other components of the culture medium, the culture medium generally contains salts, essential minerals, and antifoaming agents. The culture medium may be prepared in any manner known to those skilled in the art, for example by mixing all components together or by pre-mixing all components excluding glucose and adding them later, either individually or already pre-mixed. A commercially available culture medium may be used as a starting point, with its composition being modified at a later stage, for example when bringing the culture medium into contact with the microorganism having at least one metabolic pathway for the synthesis of 1,4-BDO from a renewable source. During fermentation, the combination comprising the microorganism and the culture medium comprising one or more sugars is maintained under conditions suitable for exploiting the metabolic pathway for the synthesis of 1,4-BDO from renewable sources. Furthermore, those skilled in the art will be able to check the progress of the process during fermentation, for example by monitoring one or more parameters and possibly acting on them to bring the process back to conditions suitable for the production of 1,4-BDO.

The production of 1,3-BG from renewable sources by fermentation takes place, for example, according to the process described in WO 2010/127319.

The fermentation broth comprising 1,3-BG from a renewable source is generally obtained by a fermentation process from a culture medium known in the art to support the growth of one or more microorganisms having at least one metabolic pathway for the synthesis of 1,3-BG under anaerobic or micro-aerobic conditions. Fermentation is carried out in batch, fed-batch or continuous mode. Anaerobic conditions are maintained by first spraying the medium with nitrogen, while micro-aerobic conditions can also be achieved with a small hole for limited aeration. The pH of the medium is typically maintained at an optimum pH by the addition of a base, such as NaOH or other bases, or an acid.

As regards the metabolic pathways for the synthesis of 1,3-BG and 1,4-BDO, these may be naturally present in the microorganism or may be created artificially, for example by altering, modifying, amplifying, eliminating or restricting metabolic pathways already present in the microorganism, inserting genetic material from one or more other organisms into the microorganism, inducing spontaneous genetic mutations, adding chemical compounds which inhibit or stimulate said metabolic pathway during the process or otherwise exploiting any genetic engineering technique. Microorganisms with metabolic pathways for the synthesis of 1,4-BDO are known to those skilled in the art and are, for example, described in Yim. H. et al., Nature Chemical Biology, Vol. 7, July 2011, pp. 445-452 (hereinafter "Yim et al. 2011") and in patent applications WO 2008/115840, WO 2009/023493, WO 2010/030711, WO 2010/071697, WO 2010/141780, WO 2010/141920, WO 2011/031897, WO 2011/047101, WO 2011/066076, WO 2012/177943, WO 2013/3204409, WO 2013/3204038, WO 2013/202623, WO 2013/203176, WO 2013/203177, WO 2013/203342, WO 2013/203440, WO 2013/203480, WO 2013/203163.

Microorganisms with metabolic pathways for the synthesis of 1,3-BG are known to those skilled in the art and are, for example, described in Kataoka, N. et al., Biosci. Biotechnol. Biochem., 2014, Vol 78, pp. 695-700 and in patent application WO 2010/127319.

The conversion of sugars into 1,3-BG and 1,4-BDO is typically less than 100% because intermediates (by-products) in the metabolic pathways used by the microorganisms to produce 1,3-BG and 1,4-BDO are also produced in addition to the two diols mentioned.

At the end of fermentation, the organisms or cells comprising the cell biomass present in the fermentation broth may be deactivated or killed. The biomass may be deactivated or cells killed by thermal means, in which case this is typically performed at a temperature of from about 50° C. to 80° C., preferably from about 60° C. to 70° C., at least at about 60° C., or at least at about 70° C., for a time of from about 1 minute to 10 minutes, preferably 2 minutes to 5 minutes, 2 minutes to 3 minutes, at least 2 minutes or at least 2.5 minutes. Such deactivation or killing of the cell biomass causes cell residues and metabolites to be released into the fermentation broth.

The broths from the fermentative production of 1,3-BG and 1,4-BDO obtained separately are mixed (step 1), resulting in a crude mixture comprising 1,3-BG and 1,4-BDO.

The term "crude mixture" within the meaning of the present invention means a broth resulting from 1,3-BG and/or 1,4-BDO fermentation processes.

For example, the crude mixture comprising 1,3-BG and 1,4-BDO comprises about 1% to 20% by weight of the sum of 1,3-BG and 1,4-BDO with respect to the total weight of said mixture and 80% to 99% by weight of the sum of water and one or more impurities (e.g., cells, salts, proteins, unconverted sugars, among those mentioned above) deriving from fermentation processes.

According to a preferred aspect, the crude mixture comprises about 5% to 18% by weight of the sum of 1,3-BG and 1,4-BDO and 82% to 95% by weight of the sum of water and one or more impurities derived from a fermentation process with respect to the total weight of said mixture.

According to a more preferred aspect, the crude mixture comprises about 10% to 15% by weight of the sum of 1,3-BG and 1,4-BDO and 85% to 90% by weight of the sum of water and one or more impurities derived from a fermentation process with respect to the total weight of said mixture.

Within the raw mixture, the ratios of 1,3-BG and 1,4-BDO are advantageously set according to the ratio of the quantities produced by the respective fermentation processes.

Impurities present in the raw mixture include, for example, one or more of the following: one or more microorganisms, cell residues, any unreacted sugars, by-products, mineral salts, metabolites and components of the culture medium that have not been assimilated or metabolised by these microorganisms.

In order to remove one or more of the impurities described above in the optional separation step (step 2) of the process according to the preferred embodiment of the invention described above, the raw mixture undergoes one or more treatments selected from decantation, centrifugation, filtration, microfiltration, nanofiltration, ultrafiltration, ion exchange, osmosis, other suitable solid/liquid separation techniques and combinations thereof.

For example, this raw mixture may be first centrifuged and then filtered, microfiltered, nanofiltered, treated with ion exchange resins and finally osmoticised.

According to one aspect of the invention, optional separation step 2) comprises one or more step operations on one or more ion exchange resins.

Said optional separation step 2) preferably comprises one or more step operations on cation exchange resins until a pH of between 4 and 2 is obtained at the output, and one or more step operations on anion exchange resins until a pH of between 8 and 11 is obtained at the output, as described in patent application WO 2019/102030.

Said cation exchange resin is generally selected from the group consisting of resins derived from strong acids (e.g. sulfonate groups) or weak acids (e.g. carboxylate groups). The cation exchange resin preferably contains functional groups selected from sulfonate groups. Non-limiting examples of cationic ion exchange resins that are useful in the process according to the invention include, for example, the resin commercially available under the brand name DOWEX® 88 or DOWEX® 88 MB.

Said anion exchange resin is generally selected from the group consisting of resins derived from strong bases (e.g. quaternary amine groups) or weak bases (e.g. tertiary amine groups). The anion exchange resin preferably contains functional groups selected from quaternary amine groups. Non-limiting examples of anion exchange resins that are useful in the process according to the invention include, for example, the resin commercially available under the brand name DOWEX® 22.

The order of the steps on the cation and anion exchange resins is not particularly limiting. One or more passes on the cation exchange resins may precede or succeed one or more passes on the anion exchange resins. Preferably, the one or more passes on the cation exchange resins precede one or more passes on the anion exchange resins.

Among the operations in optional step 2), operations may be carried out to change the solvent content (e.g. water) of the crude mixture or intermediate fractions comprising 1,3-BG and 1,4-BDO. Such operations are for example chosen from evaporation and reverse osmosis.

A mixture comprising 1,3-BG and 1,4-BDO, optionally obtained according to steps 1) and 2) described above, comprising mainly 1,3-BG, 1,4-BDO and water, is fed to step a) of the process according to the present invention. The ratios of 1,3-BG and 1,4-BDO therein are advantageously fixed according to the ratio of the amounts produced by the respective fermentation processes. Advantageously, said mixture comprises about 50% to 95% by weight of the sum of 1,3-BG and 1,4-BDO and 5% to 50% by weight of water with respect to its total weight and one or more impurities deriving from the fermentation processes.

In some embodiments, the mixture comprises about 70% to 90% by weight of the sum of 1,3-BG and 1,4-BDO and 10% to 30% by weight of water with respect to its total weight and one or more impurities deriving from a fermentation process.

In some embodiments the mixture comprises about 75% to 85% by weight of the sum of 1,3-BG and 1,4-BDO and 15% to 25% by weight of water relative to its total weight and one or more impurities derived from a fermentation process.

These impurities are, for example, included in the group consisting of one or more microorganisms, cell residues, any unreacted sugars, by-products, mineral salts, metabolites and any components of the culture medium not assimilated or metabolised by said microorganism.

In the process according to the present invention, the above-mentioned mixture comprising 1,3-BG and 1,4-BDO undergoes the steps of:

(a) removing from that mixture, by one or more distillation operations,
   i. the solvent
   ii. a heavy fraction
   iii. a light fraction
   iv. a fraction including 1,4-BDO,
  in which at least one of said fractions (iii) and (iv) comprises 1,3-BG;
(b) subjecting at least one of said fractions (iii) and (iv) comprising 1,3-BG to distillation.

The process according to the present invention therefore comprises at least two successive distillation operations.

Each of the distillation operations according to the present invention may be performed independently by employing different types and configurations of distillation columns. For example, the distillation columns in the process may comprise random-fill, structured-fill, flat-fill, random- and structured-fill, random-fill and flat-fill, or structured-fill and flat-fill sections. Structured fill columns are preferred.

Each of the distillation operations may be performed in a single column or a train of columns, or through more integrated configurations that allow more than two streams to be obtained from each column, for example with side extractions of product or the insertion of vertical baffles to minimise the number of columns and ancillary equipment.

Distillation operations according to the present process are preferably performed reducing or minimising the exposure of the compounds to high temperatures. Both the products and the impurities present therein may undergo thermal or chemical degradation due to heating during distillation. Operation of the distillation columns at reduced pressure (lower than atmospheric pressure) or vacuum is preferable as it lowers the boiling point of the mixture in the distillation column and allows the distillation column to be operated at lower temperatures. An ordinary vacuum system may be used in some or all of the distillation columns to achieve reduced pressure, or each column may have its own vacuum system.

The pressure of a distillation column may be measured at the top or in the condenser, at the bottom or at the base or anywhere in between. The different distillation columns in the process according to the invention may operate at different pressures.

The operating conditions in each stage of the process may be adjusted to the type of column(s) used.

The distillation operations in step a) of the process according to the invention make it possible to remove the solvent (i), a fraction comprising heavy compounds (ii, the so-called heavy fraction), a fraction comprising light compounds (iii, the so-called light fraction) and a fraction comprising 1,4-BDO (iv).

These components (i)-(iv) may be removed by one or more distillation operations.

Preferably solvent (i) is water.

Intermediates from the metabolic pathways used by the microorganisms (referred to as by-products) are also produced during the fermentation process for the production of 1,3-BG and 1,4-BDO, and these remain in the broth at the end of fermentation together with other organic compounds such as sugars, protein hydrolysates, proteins, amino acids, organic acids and yeast extracts (which are typically added in excess of the microorganism's actual needs and are therefore not fully utilised) and may undergo degradation processes. These organic compounds include "heavy" and "light" compounds.

By "heavy" are meant compounds with a higher boiling point than 1,4-BDO. Examples of heavy compounds are organic compounds that may have undergone a degradation process, 2-pyrrolidone and 1,6-hexanediol.

By "light" are meant compounds with a lower boiling point than 1,3-BG. Examples of light compounds are 3-hydroxy-butanal, 4-hydroxy-2-butanone, 3-hydroxybutoxy-2-butanone, 1,2-propanediol, 2,3-butanediol and gamma-butyrolactone.

In this application the operating pressure of the distillation columns is measured in absolute millibars (mbar). 1 mbar corresponds to 100 Pascal.

In step a) of the process according to the invention, according to a first aspect, solvent (i) and optionally traces of light compounds are removed from a mixture which comprises, with respect to its total weight, 60-97% by weight, preferably 80-90% by weight, of the sum of 1,3-BG and 1,4-BDO, with 1,3-BG/1,4-BDO ratios by weight that are higher than 1/99, preferably higher than 1/33, preferably higher than 1/24, more preferably higher than 1/15, even more preferably higher than 1/10 and below 99/1, preferably below 3/1, more preferably below 1/1, more preferably below 1/2, even more preferably below 1/5 and between 3% and 40% by weight, preferably between 10 and 20% by weight, of solvent (i), by a distillation operation at a temperature of between 20 and 170° C. and a head pressure of between 10 and 200 mbar, preferably between 80 and 120 mbar. Solvent (i) and optionally traces of light compounds (iii) are separated from the head. The mixture extracted from the bottom preferably comprises an amount of water less than 2000 ppm, more preferably less than 500 ppm and even more preferably less than 200 ppm.

According to another aspect, in step a) heavy fraction (ii) is removed from a mixture comprising 1,3-BG and 1,4-BDO with 1,3-BG/1,4-BDO weight ratios higher than 1/99, preferably higher than 1/33, more preferably higher than 1/24, more preferably higher than 1/15, even more preferably higher than 1/10 and below 99/1, preferably below 3/1, preferably below 1/1, more preferably below 1/2, even more preferably below 1/5 and with a quantity of water which is preferably less than 2000 ppm, more preferably less than 500 ppm and even more preferably less than 200 ppm, by means of a distillation operation at a temperature of between 100 and 170° C. and a head pressure of between 10 and 70 mbar, preferably between 20 and 50 mbar. This operation makes it possible to remove heavy fraction (ii), which comprises at least 50% by weight of heavy compounds and may comprise up to 50% by weight of 1,4-BDO, from the bottom. This fraction may be treated in a further stage to recover the 1,4-BDO it contains. The head of the column contains the stream comprising 1,3-BG and 1,4-BDO purified from heavy fraction (ii).

According to a further aspect, in step a) light fraction (iii) is removed from a mixture comprising 1,3-BG and 1,4-BDO in 1,3-BG/1,4-BDO weight ratios higher than 1/99, preferably higher than 1/33, more preferably higher than 1/24, more preferably higher than 1/15, even more preferably higher than 1/10 and below 99/1, preferably below 3/1, more preferably below 1/1, more preferably below 1/2, even more preferably below 1/5, advantageously by a distillation operation at a temperature of between 100 and 170° C., and a head pressure of between 10 and 70 mbar, preferably between 20 and 50 mbar. This operation makes it possible to remove light fraction (iii), which contains at least 1% by weight of impurities and may comprise up to 99% by weight of 1,3-BG. Said light fraction (iii) preferably comprises between 2 and 50% by weight of light materials and between 50 and 98% by weight of 1,3-BG. The bottom of the column contains mainly purified 1,4-BDO (iv), of purity >95%, preferably >98%, more preferably >99% and even more preferably >99.5% by weight. The distillation column may suitably be provided with a side extraction to allow purging of any fractions with boiling points between those of 1,4-BDO and 1,3-BG.

In step b) of the process according to the invention, possible light fraction (iii) comprising 1,3-BG is advantageously subjected to distillation at a temperature of between 20 and 170° C., and a head pressure of between 10 and 100 mbar, preferably between 30 and 60 mbar. This operation makes it possible to obtain a stream with a 1,3-BG composition of more than 95%, preferably more than 99% and even more preferably more than 99.5% by weight from the bottom. The distillation head consists mainly of light compounds and can be further treated to increase the recovery of 1,3-BG.

Alternatively, in step a) light fraction (iii) is removed from a mixture comprising 1,3-BG and 1,4-BDO in 1,3-BG/1,4-BDO weight ratios higher than 1/99, preferably higher than 1/33, more preferably higher than 1/24, more preferably higher than 1/15, even more preferably higher than 1/10 and below 99/1, preferably below 3/1, more preferably below 1/1, more preferably below 1/2, even more preferably below 1/5, advantageously by a distillation operation at a temperature of between 100 and 170° C., and a head pressure of between 10 and 100 mbar, preferably between 20 and 50 mbar. This operation makes it possible to remove light fraction (iii), which may comprise up to 95% by weight of 1,3-BG. The bottom of the column comprises 1,3-BG and 1,4-BDO.

In step b) of the process according to the invention, possible fraction (iv) comprising 1,4-BDO and 1,3-BG is advantageously subjected to distillation at a temperature of between 100 and 170° C., and a head pressure of between 10 and 100 mbar, preferably between 20 and 70 mbar. This operation makes it possible to obtain a stream with a 1,4-BDO composition of more than 98%, preferably more than 99% and even more preferably more than 99.5% by weight from the bottom. The distillation head consists mainly of 1,3-BG of purity greater than 95%, preferably greater than 98% and even more preferably greater than 99% by weight.

The distillation column may be suitably equipped with a lateral extraction to permit the purging of any fraction with a boiling point between those of 1,4-BDO and 1,3-BG.

In a preferred embodiment, step a) of the process according to the invention comprises the operations of:
    (a.1) removing solvent (i) by a first distillation,
    (a.2) removing heavy fraction (ii) by a second distillation,
    (a.3) removing light fraction (iii) by a third distillation,
       resulting in a fraction comprising 1,4-BDO (iv),
    in which at least one of said fractions (iii) and (iv) comprises 1,3-BG.

According to a preferred aspect, said light fraction (iii) comprises 1,3-BG.

According to an alternative aspect, the fraction comprising 1,4-BDO (iv) comprises 1,3-BG.

According to another preferred embodiment, the process of the present invention comprises, before step b), an optional purification treatment of the fraction (iii) comprising 1,3-BG or of the fraction (iv) comprising 1,3-BG separated in step a). The purification treatment of fraction (iii) is preferred.

According to this embodiment, the purification treatment comprises at least a hydrolysis reaction. Some of the impurities of the said fraction comprising 1,3 BG separated in step a), such as by-products deriving from fermentation and degradation processes or formed during the distillation operations of step a), in the form e.g. of acetals and/or esters, when subjected to hydrolysis form the relative aldehydes and/or ketones and the relative alcohols.

This specific embodiment is particularly advantageous since it allows to reduce or even remove the impurities which form azeotrope with 1,3-BG and 1,4-BDO, helping to further increase the recovery yields.

Preferably, the aldehydes and/or ketones thus possibly obtained are subsequently reduced to alcohols by treatment with a reducing agent, e.g. according to the process described in the Italian patent application 102020000031979.

The alcohols herein obtained after hydrolysis of acetals and/or esters, and/or obtained after reduction of aldehydes and ketones, consist mainly of 1,3-BG and/or 1,4-BDO. For example, 4-hydroxybutanal and 1,4-BDO are formed from the hydrolysis of 2-(4-hydroxybutoxy)-tetrahydrofuran.

The hydrolysis reaction may be performed according to techniques known to the skilled in the art, such as only with water, acid-catalysed, base-catalysed or catalysed by the addition of one or more enzymes.

In the case of hydrolysis with only water, the reaction is advantageously performed at high temperatures and/or pressures. Acid-catalysed hydrolysis and base-catalysed hydrolysis are advantageously performed with the addition respectively of acids and bases, or e.g. through ion exchange resins.

The added acid is preferably a strong mineral acid, which can be selected for example from orthophosphoric acid, sulfuric acid and hydrochloric acid.

The added base is preferably a strong base, which can be selected for example from NaOH, LiOH, KOH and their mixtures. Preferably the added base is NaOH.

According to an aspect of the present embodiment, at least a base-catalysed hydrolysis is performed. According to another aspect of the present embodiment, at least an acid-catalysed hydrolysis and at least a base-catalysed hydrolysis are performed.

Preferably, the hydrolysis reaction is carried out in the presence of water in an amount greater than 50% by weight, for example from 50 to 99% by weight, preferably from 55 to 95% by weight, more preferably from 75 to 90% by weight, with respect to the total weight of the aqueous solution. High amounts of water favour the hydrolysis reaction, but all the water must then be removed later, with related removal costs.

According to an aspect, the hydrolysis is carried out in the presence of and acid or of a base by maintaining the aqueous solution under stirring, preferably at a temperature between 25 and 170° C., preferably between 50 and 100° C., even more preferably between 70 and 95° C., for a time ranging from 1 minute to 240 minutes, preferably between 5 minutes and 120 minutes, even more preferably between 15 minutes and 40 minutes.

The aqueous solution obtained at the end of the hydrolysis reaction is advantageously treated to eliminate water and hydrolysis by-products, for example through one or more treatments selected from passage on a bed of ion exchange resins, activated carbon, membrane filtration, electrodialysis, flash distillation.

For example, in order to eliminate the ionic species, the aqueous solution obtained after the hydrolysis reaction can be subjected to one or more treatments with ion exchange resins, e.g. as described above for the optional separation step 2). The skilled in the art is able to choose the type of resin to be used on the basis of the hydrolysis conditions adopted.

Cation exchange resins, anionic exchange resins or a combination thereof are advantageously used. The resins are generally selected from the groups listed above for the optional separation step 2).

The aqueous solution obtained at the end of the hydrolysis reaction or, preferably, obtained after passing over the ion exchange resins or between the different passages over said resins, are then advantageously subjected to a concentration step in order to remove the water present. Said optional concentration step may be performed according to known techniques. One or more operations selected from reverse osmosis, pervaporation, evaporation, distillation, for example thermocompression evaporation or multiple effect evaporation, may advantageously be used for the purpose. Preferred techniques are evaporation or however techniques that do not require reaching too high temperatures which may deteriorate the product.

According to a more preferred embodiment, before step b) the process of the present invention further comprises subjecting the at least one of fractions (iii) and (iv) comprising 1,3-BG obtained with step a) to the further steps of:

I. hydrolysing the said at least one fraction (iii) and (iv) comprising 1,3-BG obtained with step a) in the presence of a base, obtaining an 1,3-BG aqueous solution comprising ionic species II. optionally subjecting the said aqueous solution to one or more treatments with ion exchange resins to remove ionic species from the 1,3-BG aqueous solution and III. optionally concentrating the 1,3-BG aqueous solution.

In this application, including the examples, the concentrations of the different components are expressed as % by weight.

The process according to the invention makes it possible to separate 1,3-BG and 1,4-BDO in a particularly efficient manner, obtaining a 1,4-BDO composition at a concentration of even more than 98% by weight. The 1,4-BDO composition obtained by the present process advantageously has a 1,4-BDO concentration of between 98 and 99.9% by weight, preferably between 99 and 99.9% by weight, more preferably between 99.5% and 99.9% by weight, and comprises traces of 1,3-BG in an amount greater than 1 ppm and less than or equal to 20000 ppm, preferably less than or equal to 10000 ppm, preferably less than or equal to 5000 ppm, more preferably less than or equal to 2500 ppm still more preferably less than or equal to 1000 ppm. The 1,4-BDO composition obtained by the process of the present invention can therefore be advantageously used as a source of diols in a process for producing a polyester of the diacid-diol type.

It has been found that the presence of 1,3-BG in an amount less than or equal to 20000 ppm, preferably less than or equal to 10000 ppm, preferably less than or equal to 5000 ppm, more preferably less than or equal to 2500 ppm, even more preferably less than or equal to 1000 ppm in the composition of the invention makes it possible for this composition to be used in a process for producing a polyester of the diacid-diol type (referred to below as "polyester"), without having any adverse effects on the polymerisation process. On the contrary, the use of 1,4-BDO compositions including 1,3-BG in quantities above 20000 ppm does not permit acceptable molecular masses to be reached during polymerisation under normal process conditions and, moreover, 1,3-BG and its possible by-products concentrate mainly in the esterification waters and deglycolates.

In a second aspect, the present invention therefore relates to a 1,4-BDO composition having a concentration of said 1,4-BDO greater than 98.0% by weight, preferably greater than 99% by weight, and comprising 1,3-BG in an amount less than or equal to 20000 ppm, preferably less than or equal to 10000 ppm, preferably less than or equal to 5000 ppm, more preferably less than or equal to 2500 ppm, even more preferably less than or equal to 1000 ppm.

The composition according to the invention may further comprise water, typically in an amount equal to or less than 500 ppm, preferably equal to or less than 350 ppm.

For the purposes of the present invention, the term "ppm" means a value for a substance expressed in parts per million, i.e. in milligrams (mg) per kilogram (kg) of substance.

Advantageously the 1,4-BDO composition according to the invention also comprises at least 20 ppm, preferably at least 100 ppm, more preferably at least 200 ppm and even more preferably at least 500 ppm of 1,3-BG.

When such a composition is used in a process for producing a polyester of the diacid-diol type a polyester is obtained typically comprising at least 10 ppm, preferably at least 50 ppm, more preferably at least 100 ppm, even more preferably at least 250 ppm of 1,3-BG.

Compared to a polyester produced starting from 1,4-BDO in the absence of 1,3-BG, this polyester unexpectedly shows a reduced formation of tetrahydrofuran (THF) when subjected to processing steps such as extrusion, blown film formation processes, injection moulding, thermoforming).

The amount of 1,3-BG in the 1,4-BDO composition is determined e.g. by GC-MS analysis, after calibration and preferably in the presence of an internal standard. For example, a sample of 1,4-butanediol composition is diluted with acetonitrile containing a suitable internal standard selected in such a manner that interferences with sample are avoided. Diluted sample is analysed with a Phenomenex ZB-624Plus 30 m×0.32 mm×1.80 m column using the total scan/SIM mixed mode. The concentration of 1,3-butanediol in the 1,4-butanediol composition is determined by a calibration curve obtained from standard concentration solutions against the area ratio of 1,3-butanediol and internal standard.

The amount of 1,3-BG in the polyester is determined e.g. by GC-MS analysis, after complete methanolysis to obtain methyl esters of dicarboxylic acids and free diols. The quantification is based on standard calibration and can be performed in the presence of an internal standard or an external standard, preferably in the presence of an internal standard. As preferred procedure, a suitable amount of polymer (based on expected 1,3-butanediol concentration) is treated in a stainless steel reactor with 40 ml of methanol containing 250 ppm w/v of dimethylglutarate as internal standard, and 250 ppm of zinc acetate, as methanolysis catalyst, at 220° C. for 2 h. After cooling the solution is collected and the reactor is washed with 20 ml of a solvent able to completely dissolve the methyl esters obtained (e.g. 4-methyl-2-pentanone) containing 250 ppm w/v of dimethylglutarate. Methanol solution and washing solution obtained are mixed, properly diluted and analysed in GC-MS.

Analysis is performed with a polar GC column suitable for the separation of methyl esters of dicarboxylic acids and diols, such as Phenomenex ZB-624Plus 30 m×0.32 mm×1.80 m, using the total scan/SIM mixed mode. Quantification of 1,3-butanediol is performed by a calibration curve obtained from standard concentration solutions against the area ratio of 1,3-butanediol and internal standard In a third aspect, therefore, the present invention relates to use of the composition according to the invention as a source of diols in a process for producing a polyester of the diacid-diol type.

The composition according to the invention may also advantageously be used in a process for producing a polyester-polyol, to be used as an intermediate in the synthesis of polyurethanes.

In a fourth aspect, the present invention relates to a polyester comprising:

(a) a dicarboxylic component comprising:
  (a1) 0-80% in moles, relative to the total dicarboxylic component, of units derived from at least one aromatic dicarboxylic acid, and
  (a2) 20-100% in moles, relative to the total dicarboxylic component, of units derived from at least one aliphatic dicarboxylic acid, and
(b) a diol component comprising 1,4-BDO,
  the said polyester comprising 1,3-BG in an amount of higher than 10 ppm and less than 20000 ppm.

The 1,4-BDO composition used in the process for producing a polyester according to the invention is advantageously the composition according to the invention.

The polyester according to the invention is advantageously biodegradable, preferably according to Standard EN 13432.

In addition, the polyester according to the invention has excellent mechanical properties.

The process for producing a polyester according to the invention typically comprises:

(i) preparation of an oligomer product by the esterification and/or trans-esterification reaction of a mixture comprising:
  (a) a dicarboxylic component comprising:
    (a1) 0-80% in moles, with respect to the total dicarboxylic component, of units derived from at least one aromatic dicarboxylic acid and/or its esters, salts or derivatives, and
    (a2) 20-100% in moles, with respect to the total dicarboxylic component, of units derived from at least one aliphatic dicarboxylic acid and/or one of its esters, salts or derivatives, and
  (b) a diol component comprising a 1,4-BDO composition as defined above,
(ii) polycondensation of the oligomer product obtained from step (i), and
(iii) granulation of the polyester obtained from step (ii).

The dicarboxylic acid may advantageously be obtained from a renewable source.

The dicarboxylic acid may be either aliphatic or aromatic and is preferably selected from the group consisting of aromatic dicarboxylic acids of the phthalic acid type, heterocyclic dicarboxylic aromatic compounds, saturated aliphatic dicarboxylic acids, unsaturated aliphatic dicarboxylic acids, their esters, salts and mixtures thereof.

The aromatic dicarboxylic acids of the phthalic acid type are preferably terephthalic acid or isophthalic acid, more preferably terephthalic acid, their esters, salts and mixtures thereof. The heterocyclic aromatic dicarboxylic compounds are preferably 2,5-furandicarboxylic acid, 2,4-furandicarboxylic acid, 2,3-furandicarboxylic acid, 3,4-furandicarboxylic acid, more preferably 2,5-furandicarboxylic acid, their esters, salts and mixtures thereof.

Preferably the saturated aliphatic dicarboxylic acids are selected from saturated $C_2$-$C_{24}$, preferably $C_4$-$C_{13}$, more preferably $C_4$-$C_{11}$, dicarboxylic acids, their $C_1$-$C_{24}$, preferably $C_1$-$C_4$, alkyl esters, their salts and mixtures thereof. Preferably the saturated aliphatic dicarboxylic acids are selected from: succinic acid, 2-ethylsuccinic acid, glutaric acid, 2-methylglutaric acid, adipic acid, pimelic acid, suberic acid, azelaic acid, sebacic acid, undecandioic acid, dodecandioic acid, brassylic acid and their $C_1$-$C_{24}$ alkyl esters.

The unsaturated aliphatic dicarboxylic acids are preferably selected from itaconic acid, fumaric acid, 4-methylene-pimelic acid, 3,4-bis(methylene) nonandioic acid, 5-methylene-nonandioic acid, their $C_1$-$C_{24}$, preferably $C_1$-$C_4$, alkyl esters, their salts and mixtures thereof.

The diol component may also include one or more diols other than 1,4-butanediol.

Preferably, the diol component essentially consists of the 1,4-butanediol composition according to the invention.

If present, the additional diol may be obtained from fossil or renewable sources.

If present, the additional diol is typically selected from the group consisting of saturated aliphatic diols and unsaturated aliphatic diols, aromatic diols and their mixtures.

More preferably, the saturated aliphatic diols are selected from the group consisting of 1,2-ethanediol, 1,2-propane-diol, 1,3-propanediol, 1,3-butanediol, 1,5-pentanediol, 1,6-hexanediol, 1,7-heptanediol, 1,8-octanediol, 1,9-nonane-diol, 1,10-decanediol, 1,11-undecanediol, 1,12-dodecanediol, 1,13-tridecanediol, 1,4-cyclohexanedimethanol, neopentylglycol, 2-methyl-1,3-propanediol, dianhydrosorbitol, dianhydromannitol, dianhydroiditol, cyclohexanediol, cyclohexanmethanediol, dialkylene glycols and polyalkylene glycols with a molecular weight of 100-4000 such as polyethylene glycol, polypropylene glycol and mixtures thereof.

The unsaturated aliphatic diols are most preferably selected from the group consisting of cis 2-buten-1,4-diol, trans 2-buten-1,4-diol, 2-butyn-1,4-diol, cis 2-penten-1,5-diol, trans 2-penten-1,5-diol, 2-pentyn-1,5-diol, cis 2-hexen-1,6-diol, trans 2-hexen-1,6-diol, 2-hexyn-1,6-diol, cis 3-hexen-1,6-diol, trans 3-hexen-1,6-diol, 3-hexyn-1,6-diol and mixtures thereof.

The aromatic diols are instead more preferably selected from the group consisting of 2,5-furandimethanol, 2,4-furandimethanol, 2,3-furandimethanol, 3,4-furandimethanol, more preferably 2,5-furandimethanol and mixtures thereof.

In one embodiment of the present invention the repeating units of the polyesters are 1,4-butylene dicarboxylate repeating units derived from condensation of the 1,4-butanediol composition according to the invention with mixtures comprising two or more dicarboxylic acids, preferably of the type listed above.

In a preferred embodiment, said repeating units are derived from mixtures of aromatic dicarboxylic acids and aliphatic dicarboxylic acids comprising, with respect to the total content of dicarboxylic acids:

0-65% in moles, preferably 5-60% in moles, of one or more aromatic dicarboxylic acids or heterocyclic dicarboxylic compounds, their esters or salts;

35-100% in moles, preferably 40-95% in moles, of one or more aliphatic dicarboxylic acids, their esters or salts.

In another preferred embodiment, said repeating units are derived from mixtures comprising at least two aromatic dicarboxylic acids, in turn comprising, with respect to the total content of aromatic dicarboxylic acids:

1-99% in moles, preferably 5-95% in moles, more preferably 10-80% in moles, of terephthalic acid, its esters or salts;

99-1% in moles, preferably 95-5% in moles, more preferably 90-20% in moles, of 2,5-furandicarboxylic acid, its esters or salts.

In another preferred embodiment of the present invention, said repeating units are derived from mixtures comprising at least two saturated aliphatic dicarboxylic acids, in turn comprising, with respect to the total content of aliphatic dicarboxylic acids, at least 50% in moles, preferably more than 60% in moles, more preferably more than 65% in moles of one or more saturated aliphatic dicarboxylic acids selected from the group consisting of succinic acid, adipic acid, azelaic acid, sebacic acid, brassylic acid, their $C_1$-$C_{24}$, preferably $C_1$-$C_4$ esters and mixtures thereof.

In the case of copolyesters comprising more than one diol, said copolyesters preferably contain 70% in moles, more preferably 80% in moles of 1,4-butylene dicarboxylate units. In addition to the 1,4-butylene dicarboxylate units, said copolyesters preferably comprise alkylene dicarboxylate units in which the alkylene group results from the condensation of one or more diols other than 1,4-butanediol, preferably selected from the group consisting of saturated aliphatic diols and unsaturated aliphatic diols, aromatic diols and mixtures thereof.

Examples of typical polyesters are: poly(1,4-butylene succinate), poly(1,4-butylene adipate), poly(1,4-butylene azelate), poly(1,4-butylene sebacate), poly(1,4-butylene adipate-co-1,4-butylene succinate), poly(1,4-butylene azelate-1,4-butylene succinate), poly(1,4-butylene sebacate-co-1,4-butylene succinate), poly(1,4-butylene succinate-co-1,4-butylene adipate-co-1,4-butylene azelate), poly(1,4-butylene adipate-co-1,4-butylene azelate), poly(1,4-butylene sebacate-co-1,4-butylene adipate), poly(1,4-butylene adipate-co-1,4-butylene terephthalate), poly(1,4-butylene sebacate-co-1,4-butylene terephthalate), poly(1,4-butylene azelate-co-1,4-butylene terephthalate), poly(1,4-butylene brassylate-co-1,4-butylene terephthalate), poly(1,4-butylene succinate-co-1,4-butylene terephthalate), poly(1,4-butylene adipate-co-1,4-butylene sebacate-co-1,4-butylene terephthalate), poly(1,4-butylene azelate-co-1,4-butylene sebacate-co-1,4-butylene terephthalate), poly(1,4-butylene adipate-co-1,4-butylene azelate-co-1,4-butylene terephthalate), poly(1,4-butylene succinate-co-1,4-butylene sebacate-co-1,4-butylene terephthalate), poly(1,4-butylene adipate-co-1,4-butylene succinate-co-1,4-butylene terephthalate), poly(1,4-butylene azelate-co-1,4-butylene succinate-co-1,4-butylene terephthalate), poly(1,4-butylene adipate-co-1,4-butylene-2,5-furandicarboxylate), poly(1,4-butylene sebacate-co-1,4-butylene-2,5-furandicarboxylate), poly(1,4-butylene azelate-1,4-butylene-2,5-furandicarboxylate), poly(1,4-butylene octyl-co-1,4-butylene-2,5-furan dicarboxylate), poly(1,4-butylene succinate-co-1,4-butylene-2,5-furandicarboxylate), poly(1,4-butylene adipate-co-1,4-butylene sebacate-co-1,4-butylene-2,5-furandicarboxylate), poly(1,4-butylene azelate-co-1,4-butylene sebacate-co-1,4-butylene-2,5-furandicarboxylate), poly(1,4-butylene adipate-co-1,4-butylene azelate-co-1,4-butylene-2,5-furandicarboxylate), poly(1,4-butylene succinate-co-1,4-butylene sebacate-co-1,4-butylene-2,5-furandicarboxylate), poly(1,4-butylene adipate-co-1,4-butylene succinate-co-1,4-butylene-2,5-furandicarboxylate), poly(1,4-butylene azelate-co-1,4-butylene succinate-co-1,4-butylene-2,5-furandicarboxylate). In addition to the 1,4-butylene dicarboxylate units and any other alkyl carboxylate units, the polyesters according to the present invention preferably comprise repeating units derived from at least one hydroxy acid in an amount of between 0 and 49% in moles, preferably between 0 and 30% in moles, relative to the total moles of the dicarboxylic component.

Examples of hydroxy acids are glycolic acid, hydroxy-butyric acid, hydroxycaproic acid, hydroxyvaleric acid, 7-hydroxyheptanoic acid, 8-hydroxycaproic acid, 9-hy-droxynonanoic acid, lactic acid or lactides. The hydroxy acids may be inserted into the chain as such or may also be reacted with dicarboxylic acids or diols beforehand.

The diacid-diol type polyester according to the present invention has an MFR (measured at 190° C. and 2.16 kg according to ISO standard 1133-1) in the range of 1-100 g/10 min, preferably 1-50 g/10 min, preferably 1.5-30 g/10 min, more preferably 2-20 g/10 min, even more preferably 3-10 g/10 min.

In a fifth aspect, the present invention relates to a mixture comprising:

at least one polyester according to the invention, and one or more polymers other than said polyester.

The mixture according to the present invention preferably comprises:

at least one polyester according to the invention, and 1-70% by weight, relative to the weight of polyester, of one or more polymers other than said polyester.

The mixture according to the present invention is typi-cally produced by blending, preferably in an extruder, at a temperature of between 150° C. and 250° C., with one or more polymers, typically in an amount of 1-70% by weight, relative to the weight of the polyester. Said polymers are generally selected from the group consisting of hydroxy acid polyesters, polyolefins, aromatic polyesters not comprising 1,4-butylene dicarboxylate units, polyester- and polyether-urethanes, polyurethanes, polyamides, polyamino acids, polyethers, polyureas, polycarbonates and/or one or more additives selected from among fillers, plasticisers, UV-sta-bilisers, lubricants, nucleating agents, surfactants, antistatic agents, pigments, flame retardants, compatibilising agents, polyphenols, reinforcing fillers, coupling agents, antioxi-dants, anti-mould agents, waxes, and process aids.

Among the hydroxy acid polyesters the following are preferred: poly lactic acid polyesters, poly-ε-caprolactone, polyhydroxybutyrate, polyhydroxybutyrate-valerate, poly-hydroxybutyrate-propanoate, polyhydroxybutyrate-hexano-ate, polyhydroxybutyrate-decanoate, polyhydroxybutyrate-dodecanoate, polyhydroxybutyrate-hexadecanoate, polyhydroxybutyrate-octadecanoate, poly 3-hydroxybu-tyrate-4-hydroxybutyrate.

Preferably, the hydroxy acid polyesters comprise at least 80% by weight of one or more lactic acid polyesters, relative to the total weight of the hydroxy acid polyesters. The lactic acid polyesters are preferably selected from the group con-sisting of poly L-lactic acid, poly D-lactic acid, poly D,L-lactic acid stereo complex, copolymers comprising more than 50% w/w of said lactic acid polyesters or mixtures thereof. Particularly preferred are lactic acid polyesters containing at least 95% by weight of repeating units derived from L-lactic or D-lactic acid or combinations thereof, typically having a weight-averaged molecular weight (Mw) of over 50,000 and a dynamic viscosity of between 50 and 700 Pas, preferably between 80 and 500 Pas (measured according to ASTM D3835 at T 190° C., velocity gradient 1000 s⁻¹, D 1 mm, and L/D 10), such as for example Ingeo™ Biopolymer brand products 4043D, 3251D and 6202D.

Preferably, a mixture comprising at least one polyester according to the present invention and at least one polyester from hydroxy acid comprises between 1% and 80% by weight, more preferably between 2% and 70% by weight of said polyesters from hydroxy acid with respect to the sum of the weights of the polyesters obtained by the process accord-ing to the present invention and said polyesters respectively.

Among the polyolefins, the following are preferred: poly-ethylene, polypropylene, their copolymers, polyvinyl alco-hol, polyvinyl acetate, polyethyl vinyl acetate and polyeth-ylene vinyl alcohol.

Among the aromatic polyesters, the following are pre-ferred: PET, PBT, PTT in particular with a renewables content of more than 30% and polyalkylenefurandicarboxy-lates. Among the latter, poly(1,2-ethylene-2,5-furandicar-boxylate), poly(1,3-propylene-2,5-furandicarboxylate), poly (1,4-butylene-2,5-furandicarboxylate) and mixtures thereof are particularly preferred. Examples of polyamides are poly-amide 6 and 6.6, polyamide 9 and 9.9, polyamide 10 and 10.10, polyamide 11 and 11.11, polyamide 12 and 12.12 and their combinations of the 6/9, 6/10, 6/11, 6/12 types.

The polycarbonates may be selected from the group consisting of polyethylene carbonates, polypropylene car-bonates, polybutylene carbonates, their mixtures and copo-lymers.

The polyethers may be selected from the group consisting of polyethylene glycols, polypropylene glycols, polybuty-lene glycols, their copolymers and their mixtures.

Preferably, a mixture comprising at least one polyester according to the present invention and at least one polymer selected from the group consisting of polyolefins, aromatic polyesters, polyester- and polyether-urethanes, polyure-thanes, polyamides, polyamino acids, polyethers, polyureas, polycarbonates and mixtures thereof comprises between 5% and 80% by weight, more preferably between 10% and 60% by weight, of said polymers with respect to the sum of the weights respectively of the polyesters obtained by the pro-cess according to the present invention and said polymers.

Fillers are preferably selected from the group consisting of kaolin, barytes, clay, talc, calcium and magnesium car-bonates, iron and lead carbonates, aluminium hydroxide, diatomaceous earth, aluminium sulfate, barium sulfate, silica, mica, titanium dioxide, wollastonite, starch, cellulose, chitin, chitosan, alginates, proteins such as gluten, zein, casein, collagen, gelatin, natural gums, rosinic acid and their derivatives and mixtures thereof.

The term starch covers all types of starch, in particular the following: flour, native starch, hydrolysed starch, destruc-turized starch, gelatinised starch, plasticised starch, thermo-plastic starch, biofillers comprising complexed starch or mixtures thereof. Particularly suitable according to the invention are starches such as potato, maize, tapioca and pea starch. Particularly advantageous are starches capable of being easily destructurized and having high initial molecular weights, such as for example potato and maize starch. Starch and cellulose may be present either as such or in a chemi-cally modified form, such as starch or cellulose esters with a degree of substitution between 0.2 and 2.5, hydroxypro-pylated starch, starch modified with fat chains, or as cello-phane.

With respect to destructurized starch, reference is made herein to the teachings included in patents EP 0 118 240 and EP 0 327 505, in which starch is understood to be starch which has been processed in such a way that it does not substantially show the so-called "maltese crosses" under the optical microscope in polarised light and the so-called "ghosts" under the optical microscope in phase contrast.

Advantageously, the starch is destructurized by means of an extrusion process at a temperature of between 110° C. and 250° C., preferably between 130° C. and 180° C., preferably at pressures of between 0.1 MPa and 7 MPa, preferably between 0.3 MPa and 6 MPa, preferably providing a specific energy greater than 0.1 kWh/kg during said extrusion. Said destructuring can be carried out either during step (2) of the process according to the invention or in a separate step, then feeding the starch already in destructurized form to step (2) of the process.

The starch is preferably destructurized in the presence of 1-40% by weight, with respect to the weight of starch, of one or more plasticisers selected from water and polyols having 2 to 22 carbon atoms. As far as water is concerned, this may also be the water naturally present in the starch. Among the polyols, polyols having 1 to 20 hydroxyl groups containing 2 to 6 carbon atoms, their ethers, thioethers and organic and inorganic esters are preferred. Examples of polyols include glycerol, digylcerol, polyglycerol, pentaerythritol, ethoxylated polyglycerol, ethylene glycol, polyethylene glycol, 1,2-propanediol, 1,3-propanediol, 1,4-butanediol, neopentylglycol, sorbitol monoacetate, sorbitol diacetate, sorbitol monoethoxylate, sorbitol diethoxylate, and mixtures thereof. In a preferred embodiment, the starch is destructurized in the presence of glycerol or a mixture of plasticisers comprising glycerol, more preferably comprising 2-90% by weight of glycerol. Preferably, the destructurized starch comprises 1-40% by weight, relative to the weight of starch, of plasticisers selected from those listed above. Compositions comprising destructurized starch are particularly preferred. Preferably, the starch in the mixture is present in the form of particles having a circular, elliptical or otherwise ellipse-like cross-section, having an arithmetic mean diameter of less than 1 μm, measured taking the major axis of the particle into account, and more preferably less than 0.5 μm mean diameter. As for cellulose, it may be present for example in the form of cellulose fibres or as wood flour. Advantageously, more than one filler may be used in the mixture according to the present invention. Particularly preferred are mixtures containing starch and at least one other filler.

With regard to plasticisers, one or more plasticisers selected from the group consisting of phthalates, such as, for example, diisononyl phthalate, trimellitates, such as, for example, trimellitic acid esters with $C_4$-$C_{20}$ mono-alcohols preferably selected from the group consisting of n-octanol and n-decanol, and aliphatic esters having the structure below may be present in addition to any plasticisers preferably used in preparation of the de-structured starch and described above:

$$R_1—O—C(O)—R_4—C(O)—[—O—R_2—O—C(O)—$$
$$R_5—C(O)—]_m—O—R_3$$

in which:

$R_1$ is selected from one or more of the groups made up of H, linear and branched saturated and unsaturated alkyl residues of the $C_1$-$C_{24}$ type, polyol residues esterified with $C_1$-$C_{24}$ monocarboxylic acids;

$R_2$ comprises —CH2-C(CH3)2-CH2- and alkylene $C_2$-$C_8$ groups, and consists of at least 50% in moles of said —CH2-C(CH3)2-CH2- groups;

$R_3$ is selected from one or more of the groups made up of H, linear and branched saturated and unsaturated alkyl residues of the $C_1$-$C_{24}$ type, polyol residues esterified with $C_1$-$C_{24}$ monocarboxylic acids;

$R_4$ and $R_5$, which are the same or different, comprise one or more $C_2$-$C_{22}$, preferably $C_2$-$C_{11}$, more preferably $C_4$-$C_9$ alkenes, and comprise at least 50% by moles of $C_7$ alkenes;

m is a number between 1-20, preferably 2-10, more preferably 3-7.

Preferably, in said esters at least one of groups $R_1$ and/or $R_3$ comprises polyol residues esterified with at least one $C_1$-$C_{24}$ monocarboxylic acid selected from the group consisting of stearic acid, palmitic acid, 9-ketostearic acid, 10-ketostearic acid and mixtures thereof, preferably in an amount greater than or equal to 10% in moles, more preferably greater than or equal to 20% in moles, even more preferably greater than or equal to 25% in moles with respect to the total amount of groups $R_1$ and/or $R_3$.

Examples of such aliphatic esters are described in patents EP 3 094 617 and EP 3 094 618. When present, the selected plasticisers are preferably present in an amount of between 0.2% and 20% by weight, more preferably between 0.5% and 10% by weight, relative to the total weight of the mixture. The lubricants are preferably selected from esters and metal salts of fatty acids such as, for example, zinc stearate, calcium stearate, aluminium stearate and acetyl stearate.

Preferably, when used, said lubricants are used in amounts of up to 1% by weight, more preferably up to 0.5% by weight, relative to the total weight of the mixture. Examples of nucleating agents include saccharin sodium salt, calcium silicate, sodium benzoate, calcium titanate, boron nitride, talc, zinc stearate, low molecular weight PLA. These additives are preferably added in amounts of up to 10% by weight and more preferably between 2% and 6% by weight relative to the total weight of the polyester. Pigments may also be added if necessary, for example, clays, copper phthalocyanine, titanium dioxide, silicates, iron oxides and hydroxides, carbon black, and magnesium oxide. These additives will preferably be added up to 10% by weight.

As for polyphenols, these are preferably selected from the group consisting of lignin, silybin, silidianin, isosilybin and silicristin and mixtures thereof, and are present in amounts preferably between 0.5% and 7% by weight relative to the total weight of the mixture.

In a preferred embodiment the plant-derived polyphenol advantageously comprises a mixture comprising silybin, silydianin, isosilybin and silycristin. Said mixture can advantageously be obtained by alcoholic extraction from the de-oiled cake of the seeds of the milk thistle (*Silybum marianum*) and is also commonly known commercially as silymarin. The polyesters obtained by the process according to the present invention are extremely suitable for use, alone or mixed with other polymers, in numerous practical applications for the manufacture of products such as, for example, films, fibres, non-woven fabrics, sheets, moulded, thermoformed, blown, foamed and laminated articles, including using the extrusion coating technique.

In a sixth aspect, the present invention relates to a product comprising at least one polyester according to the invention.

In one embodiment of the present invention, the product according to the invention comprises the mixture according to the invention.

The product according to the present invention is particularly suitable for use in a variety of applications including food applications.

The following are examples of products comprising at least one polyester according to the present invention:

films;

bags and liners for organic collection such as the collection of food waste and grass cuttings;

thermoformed food packaging in both single and multilayer forms, such as containers for milk, yoghurt, meat and beverages;

coatings obtained using the extrusion coating technique;

multilayer laminates with layers of paper, plastics, aluminium, metallised films;

expanded or expandable granules for the production of formed parts by sintering;

expanded and semi-expanded products including expanded blocks made from pre-expanded particles;

expanded sheets, thermoformed expanded sheets, containers made therefrom for food packaging;

containers in general for fruit and vegetables;

composites with gelatinised, de-structured and/or complexed starch, natural starch, flours, other fillers of natural, vegetable or inorganic origin, as fillers; and fibres, microfibres, composite fibres with a core made of rigid polymers such as PLA, PET, PTT, etc., and an outer shell made of the material according the invention, dablens composite fibres, fibres with different cross sections from round to multilobed, staple fibres, woven and non-woven or spun-bonded or thermobonded fabrics for the health, hygiene, agricultural and clothing sectors. They may also be used in applications to replace plasticised PVC.

The product according to the present invention is preferably a film.

The film according to the present invention may be mono- or bi-oriented.

In one embodiment of the present invention, the film according to the invention is a multilayer film with other polymer materials.

The film according to the present invention is particularly suitable for use in the agricultural sector as mulching film.

Furthermore, the film according to the present invention is particularly suitable as a stretch film for foodstuffs, for baling in agriculture and for wrapping waste.

The following examples illustrate the present invention for non-limiting purposes.

EXAMPLES

One way of separating 1,3-BG from a mixture comprising 1,3-BG and 1,4-BDO according to the invention comprises a distillation train comprising four columns as shown in FIG. 1. The distillation was simulated using Aspen Plus® software from Aspen Technology, Inc.

The composition of the feed flow (obtained by mixing the product of the fermentative production of 1,3-butanediol and the product of the fermentative production of 1,4-butanediol) is given in Table 1, as are the compositions of the intermediate flows and the operating conditions with reference to the installation in FIG. 1.

TABLE 1

|  | Units | FEED | B1 | D1 | B2 | D2 | B3 | D3 | B4 | D4 |
|---|---|---|---|---|---|---|---|---|---|---|
| Temperature | ° C. | 35.3 | 148.7 | 46.4 | 152.6 | 118.3 | 150.2 | 111.3 | 134.1 | 47.9 |
| Pressure | bar | 2.000 | 0.110 | 0.107 | 0.044 | 0.036 | 0.055 | 0.045 | 0.069 | 0.050 |
| Mass flow | kg/hr | 3000.0 | 2550.5 | 449.5 | 120.0 | 2430.5 | 2072.5 | 358.0 | 348.0 | 10.0 |
| | | | | | Fractions | | | | | |
| THF | | 171 ppm | — | 0.11% | — | — | — | — | — | — |
| WATER | | 15.0% | 400 ppm | 99.89% | — | 420 ppm | — | 0.3% | — | 10.2% |
| 3-HYDROXY-2-BUTANONE | | 72 ppm | 84 ppm | — | — | 88 ppm | — | 601 ppm | — | 2.1% |
| 4-HYDROXY-BUTYRALDEHYDE | | 428 ppm | 504 ppm | — | — | 529 ppm | — | 0.4% | — | 12.8% |
| 3-HYDROXY-BUTYRALDEHYDE | | 143 ppm | 169 ppm | — | — | 177 ppm | — | 0.1% | — | 4.3% |
| 2,3-BUTANDIOL | | 387 ppm | 455 ppm | — | — | 478 ppm | — | 0.3% | 2 ppm | 11.6% |
| 1,2-PROPANEDIOL | | 430 ppm | 506 ppm | — | — | 531 ppm | — | 0.4% | 18 ppm | 12.8% |
| GAMMA-BUTYROLACTONE | | 857 ppm | 0.10% | — | — | 0.11% | — | 0.7% | 146 ppm | 25.2% |
| 1,3-BUTANEDIOL (1,3-BG) | | 11.7% | 13.8% | — | — | 14.5% | 623 ppm | 97.8% | 99.98% | 20.9% |
| 1,4-BUTANDIOL (1,4-BDO) | | 70.7% | 83.1% | — | 40.9% | 85.2% | 99.9% | 29 ppm | 30 ppm | 0.0% |
| 2-PYRROLIDONE | | 34 ppm | 40 ppm | — | 352 ppm | 25 ppm | 29 ppm | — | — | — |
| 2-(4-HYDROXYBUTOXY)-TETRAHYDROFURAN | | 857 ppm | 0.1% | — | 2.1% | 14 ppm | 17 ppm | — | — | — |
| 1,6-HEXANEDIOL | | 343 ppm | 403 ppm | — | 0.9% | — | — | — | — | — |
| HEAVY MATERIALS | | 2.2% | 2.6% | — | 56.1% | — | — | — | — | — |

The system set up is shown in Table 2.

TABLE 2

|  | Units | COL1 | COL2 | COL3 | COL4 |
|---|---|---|---|---|---|
| Rectification stages | No. | 8 | 17 | 11 | 11 |
| Stripping stages | No. | 8 | 13 | 22 | 11 |
| Reflux ratio | — | 1 | 1.5 | 15.3 | 50 |
| Condenser pressure | mbar | 107 | 36 | 45 | 50 |

Step a)

The stream to be distilled (FEED), comprising 15% water by weight, was fed to the first distillation column (COL 1). The column had a structured fill and was operated at a head pressure of 107 mbar with a reflux ratio of 1.

The bottom of the first column (B1), with a quantity of 400 ppm of water, fed the second column (COL 2). The second column had structured filling and was operated at a head pressure of 36 mbar with a reflux ratio of 1.5.

The bottom of the second column separated the heavy fraction (B2) containing approximately 40% by weight of 1,4-BDO, while the head of the column (D2) fed the third column (COL 3). The column had a structured fill and was operated at a head pressure of 45 mbar with a reflux ratio of 15.3. The bottom of the column (B3) contained 1,4-BDO in a concentration>99.9% w/w. The column head (D3) contained mainly 1,3-BG and the light fraction.

Step b)

The head of the third column (D3) fed the fourth column (COL 4). The column had a structured fill and was operated at a head pressure of 50 mbar with a reflux ratio of 50. A light fraction (D4) containing 1,3-BG at about 21% w/w and impurities was separated from the head of the column. The purified stream of 1,3-BG (B4) was extracted from the bottom of the column, with a purity of more than 99.9% by weight.

Example 2—Preparation of a Polyester

The reagents terephthalic acid (2637 g, 15.88 mol), adipic acid (2615 g, 17.91 mol), glycerol (1.55 g, 0.017 mol) and a composition of 1,4-butanediol (purity 98.8) containing 10000 ppm of 1,3-butanediol (4563 g, 50.19 mol. MGR=1.50), were loaded into a 25 geometrical litre steel reactor provided with oil heating, a distillation column, a vacuum line with a distillates knock-down system and mechanical stirring. 250 ppm of (Tyzor TE®) were added as esterification catalyst then the reactor was sealed in nitrogen, the stirrer was switched on and the temperature was gradually raised to 220° C. over a time of 1 hour during which the water deriving from the esterification process began to distil off. The temperature was then raised to 240° C. for approximately a further hour. Distillation was allowed to proceed for 1 hour at 240° C., at the end of which the apparent conversion was 100% or more.

At the end of the esterification stage polymerisation catalyst (400 ppm of tetraorthobutyl titanate, TnBt+1000 ppm of tetraorthobutylzirconate, NBZ)) was added, the temperature of the melt was held at 240° C. and the pressure was gradually reduced to below 2 mbar over a time of approximately 30 minutes.

The reaction was continued holding the temperature of the melt at 240° C. until the desired inherent viscosity was achieved or after a maximum polymerization time of 4 hours.

The material was then discharged as strands through a spinner, cooled in a water bath and granulated into pellets. A polyester poly(1,4-butylene adipate-co-1,4-butylene terephthalate) with 47% mol of 1,4-butylene terephthalate units, and with 53% mol of adipic acid units with respect to the total dicarboxylic component, was obtained, containing 4200 ppm of 1,3-BG.

A sample of the polymer (1 g) is treated in a stainless steel reactor with 40 ml of methanol containing 250 ppm w/v of dimethylglutarate, as internal standard, and 250 ppm of zinc acetate, as methanolysis catalyst, at 220° C. for 2 h. After cooling the solution is collected and the reactor is washed with 20 ml of 4-methyl-2-pentanone containing 250 ppm w/v of dimethylglutarate. The obtained methanol solution and washing solution are mixed, properly diluted and analysed in GC-MS.

Analysis is performed with a polar GC column Phenomenex ZB-624Plus 30 m×0.32 mm×1.80 μm, using the total scan/SIM mixed mode. Quantification of 1,3-butanediol is performed by a calibration curve obtained from standard concentration solutions against the area ratio of 1,3-butanediol and internal standard

Example 3 Comparative—Preparation of a Polyester

A polyester poly(1,4-butylene adipate-co-1,4-butylene terephthalate) was prepared according to the procedure described in Example 2 but starting from a composition of 1,4-butanediol (purity 94.8%) containing 50000 ppm of 1,3-butanediol.

The MFR values of polyesters according to Examples 2 and 3 comparative are reported in Table 3.

TABLE 3

| Example | 1,3-BG in 1,4-BDO Composition [ppm] | Polymerization time [hh:mm] | MFR [g/10 min at 190° C., 2.16 kg] |
|---|---|---|---|
| 2 | 10000 | 3:10 | 4.5 |
| 3 comparative | 50000 | 4:00 | >50 |

As confirmed by the Melt Flow Rate (MFR) value, the polyester of Example 3 comparative, prepared from a 1,4-BDO composition comprising 5% 1,3-BG, did not reach an acceptable molecular mass after 4 h of polymerization time under the same process conditions.

The invention claimed is:

1. A process for the separation of 1,3-butanediol having a purity of more than 99% by weight and 1,4-butanediol having a purity of more than 98% by weight from a mixture thereof comprising a preliminary step of mixing synthesis products containing 1,3-butanediol with synthesis product containing 1,4-butanediol and the further steps of
   (a) removing from said mixture, by one or more distillation operations,
   i. solvent
   ii. a heavy fraction
   iii. a light fraction
   iv. a fraction including 1,4-butanediol,
   wherein at least one of said fractions (iii) and (iv) comprises 1,3-butanediol;
   (b) subjecting at least one of said fractions (iii) and (iv) comprising 1,3-butanediol to further distillation;
   wherein the heavy fraction means compounds with a higher boiling point than 1,4-butanediol, and the light fraction means compounds with a lower boiling point than 1,3-butanediol.

2. The process according to claim 1 wherein said synthesis products result from the production of 1,3-butanediol and 1,4-butanediol by fermentation.

3. The process according to claim 2 comprising, prior to step a) and after the preliminary step of mixing, a step of separating one or more fractions comprising solvent, by-products and/or impurities from the broths resulting from the fermentative production of 1,3-butanediol and 1,4 butanediol.

4. The process according to claim 1 comprising, before step (b), at least a hydrolysis reaction of the fraction (iii) or (iv) comprising 1,3-butanediol.

5. The process according to claim 1, wherein the mixture fed to step (a) comprises 1,3-butanediol and 1,4-butanediol having a 1,3-butanediol/1,4-butanediol weight ratio higher than 1/99 and below than 99/1.

6. The process according to claim 1, wherein the mixture fed to step (a) comprises 1,3-butanediol and 1,4-butanediol having a 1,3-butanediol/1,4-butanediol weight ratio higher than 1/33 and below than 99/1.

7. The process according to claim 1, in which the solvent (i) is water.

8. The process according to claim 1, wherein said compounds having a lower boiling point than 1,3-butanediol comprise 3-hydroxy-butanal, 4-hydroxy-2-butanone, 3 hydroxybutoxy-2-butanone, 1,2-propanediol, 2,3-butanediol and/or gamma-butyrolactone.

9. The process according to claim 1, wherein said compounds having a boiling point higher than that of 1,4-butanediol comprise organic compounds which have undergone a degradation process, 2-pyrrolidone and/or 1,6-hexanediol.

10. The process according to claim 1 wherein step a) comprises the operations of:

(a. 1) removing the solvent (i) by a first distillation, (a.2) removing the heavy fraction (ii) by a second distillation, (a.3) removing the light fraction (iii) by a third distillation to obtain a fraction comprising 1,4-butanediol (iv), in which fraction (iii) comprises 1,3-butanediol.

11. A process for producing a polyester of the diacid-diol type which comprises reacting a 1,4-butanediol composition having a concentration of the 1,4-butanediol exceeding 98.0% by weight and including 1,3-butanediol in an amount of from 20 ppm to 20000 ppm as source of diol, wherein the polyester of the diacid-diol type comprises:

(a) a dicarboxylic component comprising:

(a1) 0-80% by moles, relative to the total dicarboxylic component, of units derived from at least one aromatic dicarboxylic acid, and (a2) 20-100% by moles, relative to the total dicarboxylic component, of units derived from at least one aliphatic dicarboxylic acid, and (b) a diol component comprising 1,4-butanediol.

12. A polyester of the diacid-diol type comprising:

(a) a dicarboxylic component comprising:

(a1) 0-80% by moles, relative to the total dicarboxylic component, of units derived from at least one aromatic dicarboxylic acid, and (a2) 20-100% in by moles, relative to the total dicarboxylic component, of units derived from at least one aliphatic dicarboxylic acid, and (b) a diol component comprising 1,4-butanediol, the said polyester comprising from 10 ppm to 10000 ppm of 1,3-BG.

13. A mixture comprising:

at least one polyester of the diacid/diol type according to claim 12, and one or more polymers other than said polyester of the diacid/diol type.

14. A film comprising the mixture according to claim 13.

15. The process according to claim 2 comprising, before step (b), at least a hydrolysis reaction of the fraction (iii) or (iv) comprising 1,3-butanediol.

16. The process according to claim 2, wherein 1,3-butanediol having a purity of more than 99% by weight is obtained from step b).

17. The process according to claim 3, wherein 1,3-butanediol having a purity of more than 99% by weight is obtained from step b).

\* \* \* \* \*